US010174433B2

(12) United States Patent
Werner et al.

(10) Patent No.: US 10,174,433 B2
(45) Date of Patent: Jan. 8, 2019

(54) STANNOUS METHANESULFONATE SOLUTION WITH ADJUSTED PH

(71) Applicant: Honeywell International Inc., Morris Plains, NJ (US)

(72) Inventors: Christian N. Werner, Hannover (DE); Ronald E. H. Friedemann, Seelze (DE); Jessica Maurer, Wunstorf (DE)

(73) Assignee: Honeywell International Inc., Morris Plains, NJ (US)

( * ) Notice: Subject to any disclaimer, the term of this patent is extended or adjusted under 35 U.S.C. 154(b) by 235 days.

(21) Appl. No.: 15/039,921

(22) PCT Filed: Dec. 2, 2014

(86) PCT No.: PCT/US2014/068033
§ 371 (c)(1),
(2) Date: May 27, 2016

(87) PCT Pub. No.: WO2015/084778
PCT Pub. Date: Jun. 11, 2015

(65) Prior Publication Data
US 2017/0009362 A1  Jan. 12, 2017

Related U.S. Application Data

(60) Provisional application No. 61/912,084, filed on Dec. 5, 2013.

(51) Int. Cl.
*C23C 18/31* (2006.01)
*C25D 3/30* (2006.01)
*C25D 3/32* (2006.01)
*C07F 7/22* (2006.01)

(52) U.S. Cl.
CPC .............. *C25D 3/32* (2013.01); *C07F 7/2224* (2013.01)

(58) Field of Classification Search
CPC .............. C23C 18/31; C25D 3/30; C25D 3/32
USPC ................................. 106/1.25; 205/300, 302
See application file for complete search history.

(56) References Cited

U.S. PATENT DOCUMENTS

| | | | |
|---|---|---|---|
| 4,459,185 A | 7/1984 | Obata et al. | |
| 4,565,610 A | 1/1986 | Nobel et al. | |
| 5,039,576 A * | 8/1991 | Wilson ................. | B23K 35/262 205/254 |
| 5,162,555 A | 11/1992 | Remmers et al. | |
| 5,167,851 A | 12/1992 | Jamison et al. | |
| 5,562,814 A | 10/1996 | Kirby | |

(Continued)

FOREIGN PATENT DOCUMENTS

| | | |
|---|---|---|
| CA | 2311067 A1 | 1/2001 |
| CN | 1407141 A | 4/2003 |

(Continued)

OTHER PUBLICATIONS

International Search Report and Written Opinion issued in PCT/US2014/068033, dated Mar. 26, 2015, 12 pages.

(Continued)

*Primary Examiner* — Edna Wong
(74) *Attorney, Agent, or Firm* — Faegre Baker Daniels LLP

(57) ABSTRACT

A stannous methanesulfonate solution for tin electroplating applications and a method of forming the same are disclosed. The solution has an elevated pH. The solution also has a sufficient tin concentration for electroplating applications.

8 Claims, 2 Drawing Sheets

(56) References Cited

U.S. PATENT DOCUMENTS

| | | |
|---|---|---|
| 6,040,362 A | 3/2000 | Mine et al. |
| 6,096,414 A | 8/2000 | Young |
| 6,238,596 B1 | 5/2001 | Nguyen et al. |
| 6,339,120 B1 | 1/2002 | Misra et al. |
| 6,372,997 B1 | 4/2002 | Hill et al. |
| 6,391,442 B1 | 5/2002 | Duvall et al. |
| 6,400,565 B1 | 6/2002 | Shabbir et al. |
| 6,432,320 B1 | 8/2002 | Bonsignore et al. |
| 6,432,497 B2 | 8/2002 | Bunyan |
| 6,451,422 B1 | 9/2002 | Nguyen |
| 6,475,962 B1 | 11/2002 | Khatri |
| 6,496,373 B1 | 12/2002 | Chung |
| 6,500,891 B1 | 12/2002 | Kropp et al. |
| 6,562,180 B1 | 5/2003 | Bohin et al. |
| 6,597,575 B1 | 7/2003 | Matayabas et al. |
| 6,605,238 B2 | 8/2003 | Nguyen et al. |
| 6,610,635 B2 | 8/2003 | Khatri |
| 6,616,999 B1 | 9/2003 | Freuler et al. |
| 6,617,517 B2 | 9/2003 | Hill et al. |
| 6,620,515 B2 | 9/2003 | Feng et al. |
| 6,624,224 B1 | 9/2003 | Misra |
| 6,649,325 B1 | 11/2003 | Gundale et al. |
| 6,657,297 B1 | 12/2003 | Jewram et al. |
| 6,673,434 B2 | 1/2004 | Nguyen |
| 6,706,219 B2 | 3/2004 | Nguyen |
| 6,761,928 B2 | 7/2004 | Hill et al. |
| 6,764,759 B2 | 7/2004 | Duvall et al. |
| 6,783,692 B2 | 8/2004 | Bhagwagar |
| 6,791,839 B2 | 9/2004 | Bhagwagar |
| 6,797,382 B2 | 9/2004 | Nguyen et al. |
| 6,797,758 B2 | 9/2004 | Misra et al. |
| 6,811,725 B2 | 11/2004 | Nguyen et al. |
| 6,815,486 B2 | 11/2004 | Bhagwagar et al. |
| 6,835,453 B2 | 12/2004 | Greenwood et al. |
| 6,838,182 B2 | 1/2005 | Kropp et al. |
| 6,874,573 B2 | 4/2005 | Collins et al. |
| 6,900,163 B2 | 5/2005 | Khatri |
| 6,913,686 B2 | 7/2005 | Hilgarth |
| 6,926,955 B2 | 8/2005 | Jayaraman et al. |
| 6,940,721 B2 | 9/2005 | Hill |
| 6,946,190 B2 | 9/2005 | Bunyan |
| 6,984,685 B2 | 1/2006 | Misra et al. |
| 7,013,965 B2 | 3/2006 | Zhong et al. |
| 7,056,566 B2 | 6/2006 | Freuler et al. |
| 7,074,490 B2 | 7/2006 | Feng et al. |
| 7,078,109 B2 | 7/2006 | Hill et al. |
| 7,135,232 B2 | 11/2006 | Yamada et al. |
| 7,147,367 B2 | 12/2006 | Balian et al. |
| 7,172,711 B2 | 2/2007 | Nguyen |
| 7,241,707 B2 | 7/2007 | Meagley et al. |
| 7,244,491 B2 | 7/2007 | Nguyen |
| 7,291,396 B2 | 11/2007 | Huang et al. |
| 7,294,394 B2 | 11/2007 | Jayaraman et al. |
| RE39,992 E | 1/2008 | Misra et al. |
| 7,328,547 B2 | 2/2008 | Mehta et al. |
| 7,369,411 B2 | 5/2008 | Hill et al. |
| 7,462,294 B2 | 12/2008 | Kumar et al. |
| 7,465,605 B2 | 12/2008 | Raravikar et al. |
| 7,550,097 B2 | 6/2009 | Tonapi et al. |
| 7,572,494 B2 | 8/2009 | Mehta et al. |
| 7,641,811 B2 | 1/2010 | Kumar et al. |
| 7,682,690 B2 | 3/2010 | Bunyan et al. |
| 7,695,817 B2 | 4/2010 | Lin et al. |
| 7,700,943 B2 | 4/2010 | Raravikar et al. |
| 7,744,991 B2 | 6/2010 | Fischer et al. |
| RE41,576 E | 8/2010 | Bunyan et al. |
| 7,816,785 B2 | 10/2010 | Iruvanti et al. |
| 7,846,778 B2 | 12/2010 | Rumer et al. |
| 7,850,870 B2 | 12/2010 | Ahn et al. |
| 7,867,609 B2 | 1/2011 | Nguyen |
| 7,955,900 B2 | 6/2011 | Jadhav et al. |
| 7,960,019 B2 | 6/2011 | Jayaraman et al. |
| 8,039,961 B2 | 10/2011 | Suhir et al. |
| 8,076,773 B2 | 12/2011 | Jewram et al. |
| 8,081,468 B2 | 12/2011 | Hill et al. |
| 8,105,504 B2 | 1/2012 | Gerster et al. |
| 8,110,919 B2 | 2/2012 | Jewram et al. |
| 8,138,239 B2 | 3/2012 | Prack et al. |
| 8,223,498 B2 | 7/2012 | Lima |
| 8,308,861 B2 | 11/2012 | Rolland et al. |
| 8,324,313 B2 | 12/2012 | Funahashi |
| 8,431,647 B2 | 4/2013 | Dumont et al. |
| 8,431,655 B2 | 4/2013 | Dershem |
| 8,445,102 B2 | 5/2013 | Strader et al. |
| 8,518,302 B2 | 8/2013 | Gerster et al. |
| 8,535,478 B2 | 9/2013 | Pouchelon et al. |
| 8,535,787 B1 | 9/2013 | Lima |
| 8,586,650 B2 | 11/2013 | Zhang et al. |
| 8,587,945 B1 | 11/2013 | Hartmann et al. |
| 8,618,211 B2 | 12/2013 | Bhagwagar et al. |
| 8,632,879 B2 | 1/2014 | Weisenberger |
| 8,633,478 B2 | 1/2014 | Cummings et al. |
| 8,647,752 B2 | 2/2014 | Strader et al. |
| 8,758,892 B2 | 6/2014 | Bergin et al. |
| 8,796,068 B2 | 8/2014 | Stender et al. |
| 8,837,151 B2 | 9/2014 | Hill et al. |
| 8,865,800 B2 | 10/2014 | Stammer et al. |
| 8,917,510 B2 | 12/2014 | Boday et al. |
| 8,937,384 B2 | 1/2015 | Bao et al. |
| 9,055,694 B2 | 6/2015 | Lima |
| 9,070,660 B2 | 6/2015 | Lowe et al. |
| 9,080,000 B2 | 7/2015 | Ahn et al. |
| 9,222,735 B2 | 12/2015 | Hill et al. |
| 9,260,645 B2 | 2/2016 | Bruzda |
| 9,392,730 B2 | 7/2016 | Hartmann et al. |
| 9,481,851 B2 | 11/2016 | Matsumoto et al. |
| 9,527,988 B2 | 12/2016 | Habimana et al. |
| 9,537,095 B2 | 1/2017 | Stender et al. |
| 9,593,209 B2 | 3/2017 | Dent et al. |
| 9,593,275 B2 | 3/2017 | Tang et al. |
| 9,598,575 B2 | 3/2017 | Bhagwagar et al. |
| 2002/0018885 A1 | 2/2002 | Takahashi et al. |
| 2002/0187355 A1* | 12/2002 | Crosby .................. B32B 15/01 428/432 |
| 2003/0112603 A1 | 6/2003 | Roesner et al. |
| 2003/0151030 A1 | 8/2003 | Gurin |
| 2003/0159938 A1 | 8/2003 | Hradil |
| 2003/0203181 A1 | 10/2003 | Ellsworth et al. |
| 2003/0207064 A1 | 11/2003 | Bunyan et al. |
| 2003/0230403 A1 | 12/2003 | Webb |
| 2004/0069454 A1 | 4/2004 | Bonsignore et al. |
| 2004/0149587 A1 | 8/2004 | Hradil |
| 2004/0161571 A1 | 8/2004 | Duvall et al. |
| 2004/0206941 A1 | 10/2004 | Gurin |
| 2005/0020738 A1 | 1/2005 | Jackson et al. |
| 2005/0072334 A1 | 4/2005 | Czubarow et al. |
| 2005/0148721 A1 | 7/2005 | Tonapi et al. |
| 2005/0173255 A1* | 8/2005 | Bokisa .................. C25D 3/562 205/255 |
| 2005/0228097 A1 | 10/2005 | Zhong |
| 2005/0287362 A1 | 12/2005 | Garcia-Ramirez et al. |
| 2006/0208354 A1 | 9/2006 | Liu et al. |
| 2006/0228542 A1 | 10/2006 | Czubarow |
| 2006/0260948 A2 | 11/2006 | Zschintzsch et al. |
| 2006/0264566 A1 | 11/2006 | Cassar et al. |
| 2007/0051773 A1 | 3/2007 | Ruchert et al. |
| 2007/0097651 A1 | 5/2007 | Canale et al. |
| 2007/0131913 A1 | 6/2007 | Cheng et al. |
| 2007/0164424 A1 | 7/2007 | Dean et al. |
| 2007/0179232 A1 | 8/2007 | Collins et al. |
| 2007/0249753 A1 | 10/2007 | Lin et al. |
| 2008/0044670 A1 | 2/2008 | Nguyen |
| 2008/0141629 A1 | 6/2008 | Alper et al. |
| 2008/0291634 A1 | 11/2008 | Weiser et al. |
| 2008/0302064 A1 | 12/2008 | Rauch |
| 2009/0111925 A1 | 4/2009 | Burnham et al. |
| 2009/0184283 A1 | 7/2009 | Chung et al. |
| 2010/0048435 A1 | 2/2010 | Yamagata et al. |
| 2010/0048438 A1 | 2/2010 | Carey et al. |
| 2010/0075135 A1 | 3/2010 | Kendall et al. |
| 2010/0116674 A1* | 5/2010 | Luo .................. C25D 3/30 205/101 |
| 2010/0129648 A1 | 5/2010 | Xu et al. |
| 2010/0197533 A1 | 8/2010 | Kendall et al. |

(56) References Cited

U.S. PATENT DOCUMENTS

| | | |
|---|---|---|
| 2011/0141698 A1 | 6/2011 | Chiou et al. |
| 2011/0204280 A1 | 8/2011 | Bruzda |
| 2011/0265979 A1 | 11/2011 | Chen et al. |
| 2011/0294958 A1 | 12/2011 | Ahn et al. |
| 2011/0308782 A1 | 12/2011 | Merrill et al. |
| 2012/0060826 A1 | 3/2012 | Weisenberger |
| 2012/0195822 A1 | 8/2012 | Werner et al. |
| 2012/0253033 A1 | 10/2012 | Boucher et al. |
| 2012/0285673 A1 | 11/2012 | Cola et al. |
| 2012/0288725 A1 | 11/2012 | Tanaka et al. |
| 2013/0199724 A1 | 8/2013 | Dershem |
| 2013/0248163 A1 | 9/2013 | Bhagwagar et al. |
| 2013/0265721 A1 | 10/2013 | Strader et al. |
| 2013/0288462 A1 | 10/2013 | Stender et al. |
| 2014/0190672 A1 | 7/2014 | Swaroop et al. |
| 2015/0125646 A1 | 5/2015 | Tournilhac et al. |
| 2015/0275060 A1 | 10/2015 | Kuroda et al. |
| 2015/0279762 A1 | 10/2015 | Lowe et al. |
| 2016/0160104 A1 | 6/2016 | Bruzda et al. |
| 2017/0137685 A1 | 5/2017 | Liu et al. |

FOREIGN PATENT DOCUMENTS

| | | |
|---|---|---|
| CN | 1456710 A | 11/2003 |
| CN | 1549875 A | 11/2004 |
| CN | 101067030 A | 11/2007 |
| CN | 101090922 B | 12/2007 |
| CN | 101445627 A | 6/2009 |
| CN | 101735619 B | 6/2010 |
| CN | 101835830 B | 9/2010 |
| CN | 102134474 B | 7/2011 |
| CN | 102341474 B | 2/2012 |
| CN | 102627943 A | 8/2012 |
| CN | 102348763 B | 4/2013 |
| CN | 103087389 A | 5/2013 |
| CN | 103102689 A | 5/2013 |
| CN | 103131138 B | 6/2013 |
| CN | 103254647 A | 8/2013 |
| CN | 103333447 A | 10/2013 |
| CN | 103409116 B | 11/2013 |
| CN | 103436027 B | 12/2013 |
| CN | 103709757 A | 4/2014 |
| CN | 103773322 A | 5/2014 |
| CN | 103849356 A | 6/2014 |
| CN | 103865271 B | 6/2014 |
| CN | 104098914 A | 10/2014 |
| CN | 104140678 B | 11/2014 |
| CN | 104449506 A | 3/2015 |
| CN | 104497574 A | 4/2015 |
| CN | 104804705 A | 7/2015 |
| CN | 104861661 A | 8/2015 |
| CN | 105111750 A | 12/2015 |
| CN | 105349113 A | 2/2016 |
| CN | 105838322 A | 8/2016 |
| CN | 105980512 A | 9/2016 |
| EP | 1224669 B1 | 7/2002 |
| EP | 1149519 B1 | 11/2004 |
| EP | 1514956 B1 | 3/2005 |
| EP | 1629059 B1 | 3/2006 |
| EP | 2194165 A1 | 6/2010 |
| FR | 2848215 A1 | 6/2004 |
| GB | 2508320 B | 5/2014 |
| JP | 57027188 B | 6/1982 |
| JP | 3662715 B2 | 1/1991 |
| JP | 02611364 B2 | 5/1997 |
| JP | 2000143808 A | 5/2000 |
| JP | 2001139818 A | 5/2001 |
| JP | 4016326 B2 | 12/2007 |
| JP | 2008063412 A | 3/2008 |
| JP | 5269366 B2 | 3/2009 |
| JP | 5137538 B2 | 6/2009 |
| JP | 2009138036 A | 6/2009 |
| JP | 4288469 B2 | 7/2009 |
| JP | 5607298 B2 | 3/2010 |
| JP | 5390202 B2 | 8/2010 |
| JP | 2010248277 A | 11/2010 |
| JP | 5318733 B2 | 6/2011 |
| JP | 2011165792 A | 8/2011 |
| JP | 5687167 B2 | 4/2013 |
| JP | 5463116 B2 | 4/2014 |
| JP | 5944306 B2 | 7/2014 |
| JP | 5372270 B1 | 9/2014 |
| JP | 2014194006 A | 10/2014 |
| KR | 100479857 B1 | 7/2003 |
| KR | 20070116654 A | 12/2007 |
| TW | 201527309 A | 7/2015 |
| WO | WO0120618 A1 | 3/2001 |
| WO | 2003064148 A1 | 8/2003 |
| WO | 2004008497 A2 | 1/2004 |
| WO | 2005119771 A1 | 12/2005 |
| WO | 2007027670 A1 | 3/2007 |
| WO | 2008014171 A2 | 1/2008 |
| WO | 2008121491 A1 | 10/2008 |
| WO | 2008121970 A1 | 10/2008 |
| WO | 2009032212 A1 | 3/2009 |
| WO | 2013191116 A1 | 12/2013 |
| WO | 2014160067 A1 | 10/2014 |
| WO | 2015179056 A1 | 11/2015 |
| WO | 2016004565 A1 | 1/2016 |
| WO | 206103424 A1 | 6/2016 |

OTHER PUBLICATIONS

Vlartyak et al., On the oxidation of tin(II) in methanesulfonate solutions and the role of sulfate, Galvanotechnik (2005), 96(3), 594-601 (Abstract).

"Hi-Flow 225F-AC Reinforced, Phase Change Thermal Interface Material," The Bergquist Company, 1 page, available at least as early as the filing of the present application.

"Therm-A-Gap HCS10,569,570,579 and 580 Thermally Conductive Gap Filler Pads," Parker Chomerics, Engineering Your Success, pp. 11-12, available at least as early as the filing of the present application.

Aranzabe, Estibaliz, et al. "More than Color: Pigments with Thermal Storage Capacity; Processing and Degradation Behavior." Advances in Materials Physics and Chemistry, 5:171-184, 2015.

Extended European Search Report issued in EP Application 14867847.7, dated Jun. 26, 2017, 7 pages.

Gowda, Arun, et al. "Choosing the Right Thermal Interface Material." Solid State Technology, Insights for Electronics Manufacturing, Online Blog, 9 pages, 2005. Retrieved May 25, 2017 from the Internet <http://electroiq.com/blog/2005/03/choosing-the-right-thermal-interface-material/.

International Search Report and Written Opinion issued in PCT/CN2014/081724. dated Apr. 1, 2015, 12 pages.

International Search Report and Written Opinion issued in PCT/CN2014/093138, dated Sep. 6, 2015, 8 pages.

International Search Report and Written Opinion issued in PCT/CN2016/101874, dated Apr. 28, 2017, 12 pages.

Ramaswamy, C., et al. "Phase Change Materials as a Viable Thermal Interface Material for High-Power Electronic Applications." The Ninth Intersociety Conference on Thermal and Thermomechanical Phenomena in Electronic Systems, IEEE, 2:687-691, 2004.

Search Report issued in CN application 201480066502.2, dated May 18, 2017, 2 pages.

International Search Report and Written Opinion issued in PCT/US2017/041498, dated Oct. 20, 2017, 10 pages.

Ping, Ding, et al. "Preparation and Application Research of Novel Silicone Gel for High-Power IGBT." Insulating Materials, 47(2):52-55, Chinese text with English translation of Abstract, 2014.

* cited by examiner

STANNOUS METHANESULFONATE SOLUTION WITH ADJUSTED PH

CROSS-REFERENCE TO RELATED APPLICATION

This application is the U.S. national stage of PCT/US2014/068033, published as WO 2015/084778, filed Dec. 2, 2014, which claims the benefit under Title 35, U.S.C. § 119(e) of U.S. Provisional Patent Application Ser. No. 61/912,084, filed Dec. 5, 2013, each of which is hereby incorporated by reference herein in its entirety.

FIELD OF THE INVENTION

The present disclosure relates to tin electroplating. In particular, the present disclosure relates to a stannous methanesulfonate solution for tin electroplating applications and a method of forming the same.

DESCRIPTION OF THE RELATED ART

With reference to FIG. 1, electroplating or electrochemical deposition involves coating dissolved metal ions from an electrolytic solution 10 onto a substrate 12 (e.g., a semiconductor wafer) by applying a voltage between the substrate 12 (i.e., cathode) and a counter electrode 14 (i.e., anode). The substrate 12 and the counter electrode 14 are both located in a vessel 16 containing the electrolyte 10. A membrane or separator 18 is provided between the substrate 12 and the counter electrode 14. The coating is achieved through the reduction of metal ions in the electrolyte 10 by the negatively charged substrate 12 (i.e., cathode), which deposits elemental metal onto the substrate 12.

In tin electroplating applications, methanesulfonic acid (MSA) solutions are commonly used as the electrolyte. MSA has certain advantages over other types of electrolytes (e.g., fluoroborate, sulfate, halogen and phenolsulfonic acid (PSA) chemistries) in that it is: less corrosive than fluoroborate and sulfate chemistries; less likely to exhibit Sn(II) to Sn(IV) conversion; and less costly than fluoroborate, PSA, and halogen chemistries for effluent treatment and disposal (i.e., more environmentally friendly). Also, MSA is highly soluble in water. Further, MSA is a strong acid that provides high conductivity, high current densities, and high throwing power and covering power. *Modern Electroplating*, 4th Edition, eds. M. Schlesinger and M. Paunoic, Wiley-Interscience, New York, 2000.

Normally, the operating pH of MSA is less than 1 for tin electroplating applications. However, in certain applications, such as applications involving specialty membranes, this operating pH may be too low.

SUMMARY OF THE INVENTION

The present disclosure provides a stannous methanesulfonate solution for tin electroplating applications and a method of forming the same. The solution has an elevated pH. The solution also has a sufficient tin concentration for electroplating applications.

In one form thereof, the present disclosure provides a solution including at least one stannous methanesulfonate species, the solution having a tin concentration of about 15 g/L or more, and a pH of about 1.50 to about 2.20.

In certain embodiments, the tin concentration is about 15 g/L to about 100 g/L, or about 56 g/L to about 82 g/L, or about 58 g/L to about 62 g/L.

In certain embodiments, the pH is about 1.60 to about 2.00, such as about 1.80, or about 1.50 to about 1.70.

In certain embodiments, the solution has a density of about 1.1 g/mL.

In certain embodiments, the at least one stannous methanesulfonate species comprises $Sn(CH_3SO_3)_2$.

In certain embodiments, the solution further includes a second stannous methanesulfonate species comprising at least one of $Sn(OH)(CH_3SO_3)$ and $Sn(O)(CH_3SO_3)$.

In another form thereof, the present disclosure provides a method for forming a stannous methanesulfonate solution including reacting tin with an aqueous methanesulfonic acid solution in the presence of an oxygen-containing gas to produce an aqueous stannous methanesulfonate solution having a pH; and adjusting the pH of the aqueous stannous methanesulfonate solution to an adjusted pH of about 1.50 to about 2.20 by adding a pH-adjusting agent to the aqueous stannous methanesulfonate solution.

In certain embodiments, the pH-adjusting agent is a base.

In certain embodiments, the pH-adjusting agent is one of a metal oxide, such as tin oxide, a carbonate, and a hydroxide, such as sodium hydroxide.

In certain embodiments, the adjusted pH is about 1.80.

In certain embodiments, the method further includes diluting the aqueous stannous methanesulfonate solution to a tin concentration of about 56 g/L to about 82 g/L.

In yet another form thereof, the present disclosure provides a stannous methanesulfonate species comprising $Sn_xR_z(CH_3SO_3)_y$, wherein x is 1, y is less than 2, and z is greater than 0.

In certain embodiments, the species comprises at least one of $Sn(OH)(CH_3SO_3)$ and $Sn(O)(CH_3SO_3)$.

In certain embodiments, R comprises at least one of a hydroxy group or and an oxo group.

In certain embodiments, the Sn has an alpha content less than about 0.002 alpha counts/hour/cm$^2$.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein.

DETAILED DESCRIPTION

Figure 1:
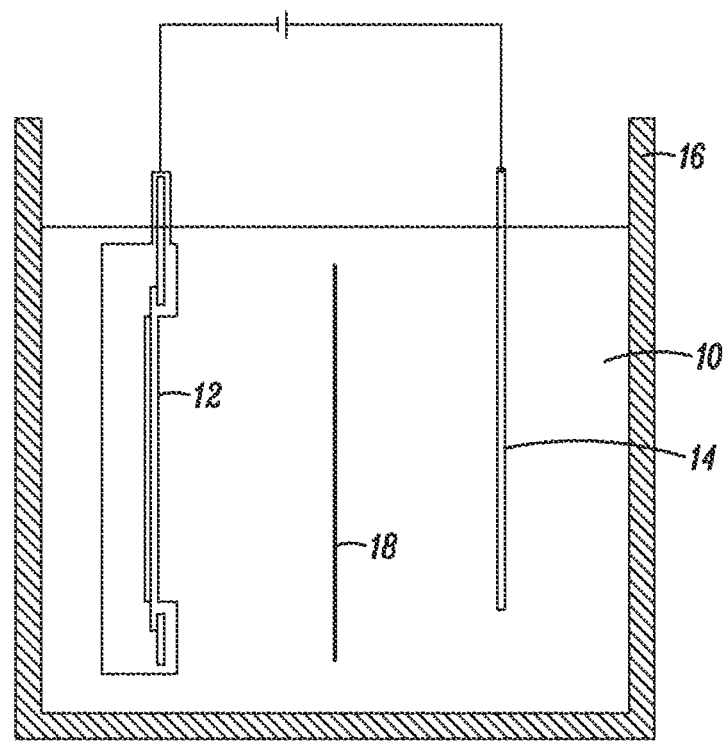
FIG. 1 is a schematic view of a tin electroplating cell.

The present disclosure provides a stannous methanesulfonate solution having an elevated pH and a method of forming the same.

1. First Reaction Stage for Preparation of Stannous Methanesulfonate
Solution

During a first reaction stage, tin (Sn) is reacted with an aqueous methanesulfonic acid (MSA or $CH_3SO_3H$) solution in the presence of an oxygen-containing gas (e.g., air) to produce an aqueous stannous methanesulfonate ($Sn(MSA)_2$ or $Sn(CH_3SO_3)_2$) solution, according to Reaction (1) below. In one embodiment, the reaction is performed in a normal atmospheric environment. In another embodiment, the reaction is performed in a modified environment having a higher oxygen content than the normal atmospheric environment.

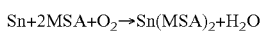

$$Sn+2MSA+O_2 \rightarrow Sn(MSA)_2+H_2O \qquad (1)$$

The temperature of the first reaction stage may vary. For example, the first reaction stage may be carried out at a temperature as low as about 20, 40, or 60° C. and as high as about 80, 100, or 120° C., or within any range delimited by any pair of the foregoing values.

The Sn reactant used in the first reaction stage may have a low alpha content. For example, the Sn reactant may have an alpha content less than about 0.002, 0.0015, or 0.001 alpha counts/hour/cm$^2$. The alpha content may be measured using an alpha particle detector, such as the UltraLo-1800 Alpha Particle Counter available from XIA LLC of Hayward, Calif. In embodiments where the Sn in the solution is electroplated for electronic device packaging or other electronic manufacturing applications, the low alpha content of the Sn may reduce the risk of single-event upsets ("SEUs"), often referred to as soft errors or soft error upsets. The Sn reactant may be provided in the form of a powder or pellets, for example.

In certain embodiments, the MSA reactant used in the first reaction stage may be added in excess such that free MSA remains in the solution after the first reaction stage. The MSA content of the aqueous MSA solution used in the first reaction stage may vary. For example, the aqueous MSA solution may have a MSA content as low as about 50, 55, 60, or 65 weight % and as high as about 70, 75, or 80 weight %, or within any range delimited by any pair of the foregoing values.

The Sn(MSA)$_2$ solution produced during the first reaction stage may have a Sn(II) concentration as low as about 18, 19, 20, or 21 weight % and as high as about 22, 23, 24, or 25 weight %, or within any range delimited by any pair of the foregoing values. In certain embodiments, the Sn(II) concentration may be less than 18 weight % or more than 25 weight %.

The Sn(MSA)$_2$ solution produced during the first reaction stage may have a highly acidic pH. In certain embodiments, the pH of the solution may be about 1.0 or less, such as about 0.8, 0.9, or 1.0, for example.

An exemplary Sn(MSA)$_2$ solution prepared according to Reaction (1) above includes Tin(II) Methanesulfonate Solution 300, Product No. 14557, CAS No. 53408-94-9, which is available from Honeywell Specialty Chemicals of Seelze, Germany.

Additional information regarding the preparation of Sn(MSA)$_2$ is found in U.S. Pat. No. 5,162,555 to Remmers et al., the entire disclosure of which is expressly incorporated herein by reference.

2. Second Reaction Stage for pH Adjustment

During a second reaction stage, a pH-adjusting agent may be added to the highly acidic Sn(MSA)$_2$ solution from the first reaction stage to increase the pH to a more neutral pH. When added to the highly acidic Sn(MSA)$_2$ solution from the first reaction stage, the pH-adjusting agent may be basic in nature.

The pH-adjusting agent may be classified as a Brønsted base that accepts hydrogen ions (H$^+$) in the solution and/or a Lewis base that donates a pair of electrons in the solution. Suitable pH-adjusting agents include metal oxides, such as tin oxide (SnO), and carbonates, such as sodium carbonate (Na$_2$CO$_3$), for example.

The pH-adjusting agent may also be classified more narrowly as an Arrhenius base that produces hydroxide ions (OH$^-$) in the solution. Suitable pH-adjusting agents include sodium hydroxide (NaOH), potassium hydroxide (KOH), and other alkaline or alkali earth metal hydroxides, for example.

In embodiments where the pH-adjusting agent contributes additional Sn to the solution, such as when the pH-adjusting agent is SnO, free MSA may be present in the solution as excess from the first reaction stage to react with the additional Sn and to maintain the Sn in solution. By contrast, in embodiments where the pH-adjusting agent does not contribute additional Sn to the solution, such as when the pH-adjusting agent is NaOH, free MSA may be unnecessary in the solution.

The temperature of the second reaction stage may vary. For example, the second reaction stage may be carried out at a temperature as low as about 20, 40, or 60° C. and as high as about 80, 100, or 120° C., or within any range delimited by any pair of the foregoing values.

As discussed above, the first reaction stage may produce the Sn$_x$R$_z$(MSA)$_y$ species of Sn(MSA)$_2$, wherein x is 1, y is 2, and z is 0. Without wishing to be bound by theory, the present inventors believe that certain solutions of the present disclosure may contain soluble Sn$_x$R$_z$(MSA)$_y$ species in addition to Sn(MSA)$_2$. Adding the pH-adjusting agent during the second reaction stage may form hydroxide-anions (OH$^-$) and/or oxo-anions (O$^{2-}$) in the solution. In certain embodiments, such anions may cause Sn$_x$R$_z$(MSA)$_y$ species other than Sn(MSA)$_2$ to form in the solution. As a result, not all of the Sn ions in the solution may be present in the form of Sn(MSA)$_2$, and at least some of the Sn ions in the solution may be present in the form of other Sn$_x$R$_z$(MSA)$_y$ species.

Figure 2:
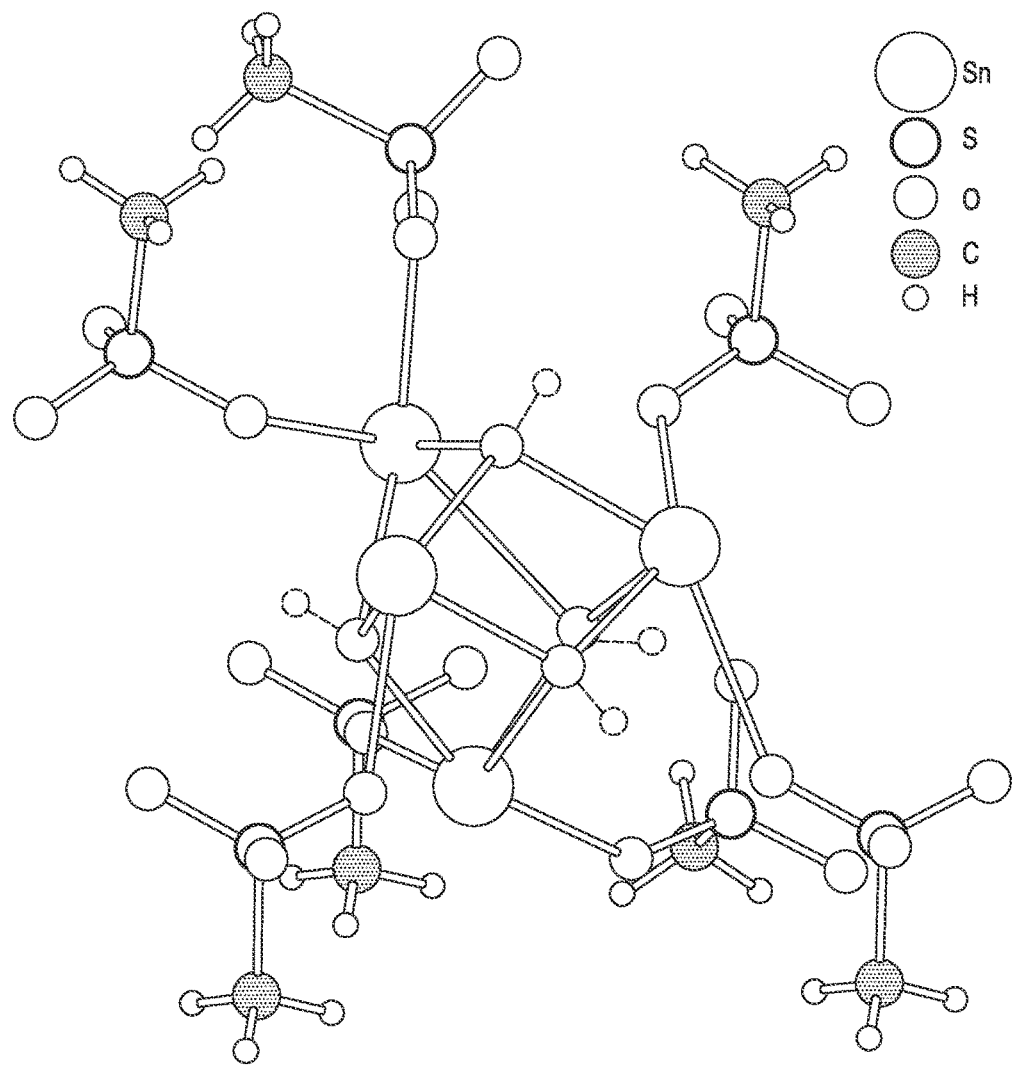
FIG. 2 shows exemplary crystal structures for various $Sn_xR_z(MSA)_y$ species.

The other Sn$_x$R$_z$(MSA)$_y$ species produced during the second reaction stage may contain reduced levels of MSA compared to Sn(MSA)$_2$, such that y is less than 2. Also, z may be greater than 0, so the Sn$_x$R$_z$(MSA)$_y$ species may contain one or more bridging R atoms or groups, including oxygen atoms (O), hydroxy groups (OH), or other bridging atoms or groups. One such species may include oxo-stannous methanesulfonate (Sn(O)MSA or Sn(O)(CH$_3$SO$_3$)), for example, wherein x is 1, y is 1, and z is 1 and the bridging R atom is O. Without wishing to be bound by theory, Sn(O)MSA may have the crystal structure shown in solid lines in FIG. 2, where 4 Sn atoms and 4 MSA groups are bridged by 4 corresponding O atoms. 4 neighboring MSA groups are also shown in FIG. 2. Another such species may include hydroxy-stannous methanesulfonate (Sn(OH)MSA or Sn(OH)(CH$_3$SO$_3$)), for example, wherein x is 1, y is 1, and z is 1 and the bridging R group is OH. Without wishing to be bound by theory, each of the 4 bridging O atoms may include a corresponding H atom, as shown in phantom lines in FIG. 2, to arrive at the crystal structure of Sn(OH)MSA. Because Sn is usually present in divalent form (+2), the present inventors believe that Sn(OH)MSA, where Sn is in divalent form (+2), would be more prevalent than the Sn(O)MSA, where SD is in trivalent form (+3). Yet another such species may include a blend of oxo-stannous methanesulfonate (Sn(O)MSA) and hydroxy-stannous methanesulfonate (Sn(OH)MSA) having both O and OH as bridging R groups.

In embodiments where the pH-adjusting agent contributes additional Sn to the solution, such as when the pH-adjusting agent is SnO, the present inventors believe that the additional Sn ions from the second reaction stage may react with free MSA left over from the first reaction stage to produce Sn(OH)MSA according to Reaction (2) below (See also Example 1 below).

$$SnO+[Sn(MSA)_2+MSA] \rightarrow Sn(MSA)_2+Sn(OH)MSA \quad (2)$$

By contrast, in embodiments where the pH-adjusting agent does not contribute additional Sn to the solution, such as when the pH-adjusting agent is NaOH, the solution may lack additional Sn ions from the second reaction stage and excess MSA from the first reaction stage, so the present inventors believe that Sn(OH)MSA may not form in the solution (See also Example 2 below).

It is within the scope of the present disclosure that the above-described first and second reaction stages may be combined and performed simultaneously.

3. Clarification

The $Sn(MSA)_2$ solution may be clarified to remove precipitates, undissolved residues, and other solid substances from the liquid $Sn(MSA)_2$ solution. Such undissolved residues may include excess amounts of the pH-adjusting agent added to the $Sn(MSA)_2$ solution during the second reaction stage, for example.

In certain embodiments, the clarification stage may involve adding activated charcoal to the solution and then filtering the solution through a paper filter or another suitable filter, for example. In other embodiments, the clarification stage may involve centrifugation or gravity settling, for example.

After clarification, the solution may appear substantially clear and free of visible precipitates, undissolved residues, and other solid substances. The solution may have a solids content less than about 0.10, 0.05, or 0.01 weight %, for example. The solution may be colored (e.g., yellow).

Although the clarification stage follows the first and second reaction stages in this description, the order of these steps may vary. It is also within the scope of the present disclosure that the solution may be subjected to more than one clarification stage. For example, the solution may be subjected to a first clarification stage after the first reaction stage and to a second clarification stage after the second reaction stage.

4. Dilution

The $Sn(MSA)_2$ solution may be diluted with varying amounts of water (e.g., distilled water) to achieve a desired Sn(II) concentration and/or a desired pH.

The desired Sn(II) concentration in the solution may be about 15 g Sn(II)/L to about 100 g Sn(II)/L. For example, the desired Sn(II) concentration in the solution may be as low as about 15, 20, 25, 30, 35, 40, 45, 50, or 55 g Sn(II)/L and as high as about 60, 65, 70, 75, 80, 85, 90, 95, or 100 g Sn(II)/L, or within any range delimited by any pair of the foregoing values. In certain embodiments, the desired Sn(II) concentration in the solution may be about 56 g Sn(II)/L to about 82 g Sn(II)/L. For example, the desired Sn(II) concentration in the solution may be as low as about 56, 58, 60, 62, 64, 66, or 68 g Sn(II)/L and as high as about 70, 72, 74, 76, 78, 80, or 82 g Sn(11)/L, or within any range delimited by any pair of the foregoing values. The desired Sn(II) concentration in the solution may be about 58 to about 62 g Sn(II)/L, for example.

The desired Sn(II) concentration may also be expressed as a weight percentage. For a solution having a density of 1.1 g/mL and a Sn(II) concentration of about 56 g Sn(II)/L to about 82 g Sn(II)/L, for example, the Sn(II) concentration may be about 5.1 weight % (which corresponds to 56 g Sn(II)/L) to about 7.5 weight % Sn(II) (which corresponds to 82 g Sn(II)/L). The weight percentage range may vary as the density of the solution varies.

The desired pH may be about 1.50 to about 2.20. For example, the desired pH may be as low as about 1.50, 1.55, 1.60, 1.65, 1.70, 1.75, or 1.80 and as high as about 1.85, 1.90, 1.95, 2.00, 2.05, 2.10, 2.15, or 2.20, or within any range delimited by any pair of the foregoing values. In certain embodiments, the desired pH may be about 1.60 to about 2.00, such as about 1.80.

Exemplary solutions are presented in Table 1 below. In embodiments where the pH-adjusting agent contributes additional Sn to the solution, such as when the pH-adjusting agent is SnO, the pH of the solution may be limited by the amount of additional Sn that the solution is capable of dissolving. In Table 1, for example, a solution having a Sn(II) concentration of about 56 g Sn(II)/L to about 82 g Sn(II)/L may be capable of reaching a pH value in the range of about 1.50 to about 1.70 when the pH-adjusting agent is SnO (See Solution A below). By contrast, in embodiments where the pH-adjusting agent does not contribute additional Sn to the solution, such as when the pH-adjusting agent is NaOH, the solution may be capable of reaching a broader range of pH values while maintaining the Sn in solution, in Table 1, for example, a solution having a Sn(II) concentration of about 56 g Sn(II)/L to about 82 g Sn(II)/L may be capable of reaching a pH value in the range of about 1.50 to about 2.20 when the pH-adjusting agent is NaOH (See Solution B below).

TABLE 1

| Solutions | pH-Adjusting Agent | Sn(II) Concentration (g/L) | pH |
| --- | --- | --- | --- |
| A | SnO | 56-82 | 1.50-1.70 |
| B | NaOH | 56-82 | 1.50-2.20 |

Other exemplary solutions are presented in Table 2 below. In embodiments where the pH-adjusting agent contributes additional Sn to the solution, such as when the pH-adjusting agent is SnO, the pH of the solution is inversely related to the Sn(II) concentration of the solution. This trend is shown in Table 2 below. For example, as the desired pH of the solution increases, the maximum Sn(II) concentration of the solution decreases (See Solution A5 below). Above this maximum Sn(II) concentration, the solution may become unstable and Sn(II) may precipitate out of the solution. Similarly, as the desired Sn(II) concentration of the solution increases, the maximum pH of the solution decreases (See Solution A1 below). Above this maximum pH, the solution may become unstable and Sn(II) may precipitate out of the solution. By contrast, in embodiments where the pH-adjusting agent does not contribute additional Sn to the solution, such as when the pH-adjusting agent is NaOH, the solution may be capable of reaching various pH values at each Sn(II) concentration.

TABLE 2

| Solution | pH-Adjusting Agent | Sn(II) Concentration (g/L) | Density (g/mL) | Sn(II) Concentration (weight %) | pH |
| --- | --- | --- | --- | --- | --- |
| A1 | SnO | 78.5 | 1.106 | 7.1 | 1.58 |
| A2 | SnO | 70.4 | 1.100 | 6.4 | 1.63 |
| A3 | SnO | 44.4 | 1.056 | 4.2 | 1.76 |
| A4 | SnO | 35.4 | 1.042 | 3.4 | 1.81 |
| A5 | SnO | 17.4 | 1.023 | 1.7 | 1.95 |
| B1 | NaOH | 80.6 | 1.152 | 7.0 | 1.82 |
| B2 | NaOH | 57.7 | 1.109 | 5.2 | 1.90 |
| B3 | NaOH | 44.4 | 1.083 | 4.1 | 1.98 |
| B4 | NaOH | 19.7 | 1.037 | 1.9 | 2.12 |

The dilution stage may also promote stability of the solution by preventing the $Sn(MSA)_2$ from precipitating out of the solution during cooling and subsequent storage. In certain embodiments, the solution may remain stable for at least about 30 days, 60 days, 90 days, or more, for example.

In certain embodiments, the desired properties may be achieved without requiring the addition of other elements or additives besides water which could hinder the stability of Sn in the solution or the transfer efficiency of Sn through a membrane of an electroplating cell. For example, the desired properties may be achieved without requiring the addition of chelating agents, which may cause Sn to precipitate out of the solution at the desired pH levels of the present disclosure. The desired properties may also be achieved without requiring the addition of antioxidants, stabilizers, surfactants, or complexing agents, for example. Therefore, in one embodiment, the solution may lack additives such as chelating agents, antioxidants, stabilizers, surfactants, or complexing agents. As used herein, the solution may lack an additive if the additive is present in an amount less than about 0.01 weight %. In other embodiments, the solution may contain one or more additives such as chelating agents, antioxidants, stabilizers, surfactants, or complexing agents.

Metals other than tin may be present in the solution in small amounts. Such metals may include iron (Fe), cobalt (Co), copper (Cu), nickel (Ni), and lead (Pb), for example. In aggregate, these other metals may be present in the solution in amounts less than about 25, 15, or 5 ppm. The solution may also contain small amounts of sulfate ($SO_4$) species, chlorine (Cl) species, and other species, for example.

Although the dilution stage follows the first and second reaction stages and the clarification stage in this description, the order of these steps may vary. It is also within the scope of the present disclosure that the solution may be subjected to more than one dilution stage. For example, the solution may be subjected to a first dilution stage after the first reaction stage and to a second dilution stage after the second reaction stage.

EXAMPLES

The following non-limiting Examples illustrate various features and characteristics of the present invention, which is not to be construed as limited thereto.

Example 1

Tin Oxide as pH-Adjusting Agent

During a first reaction stage, Sn was reacted with an aqueous MSA solution in the presence of air to produce an aqueous $Sn(MSA)_2$ solution. The solution contained 21.3 weight % Sn(II) and 5.8 weight % free MSA.

During a first dilution stage, 5.5 kg of the $Sn(MSA)_2$ solution was diluted with 0.38 kg (380 g) of distilled water to reach about 20 weight % Sn(II).

During a second reaction stage, and within 20 minutes of the first dilution stage, 0.67 kg (670 g) of SnO was added to the diluted $Sn(MSA)_2$ solution. An initial portion of SnO dissolved into the solution. A subsequent, excess portion of SnO remained un-reacted in the solution. With the addition of SnO, the solution contained 26.7 weight % Sn(II).

During a second dilution stage, the solution was diluted with 22 kg of distilled water. The diluted solution was stirred for 2 hours.

During a clarification stage, 0.9 weight % of activated charcoal was added to the solution. After 30 minutes of additional stirring, the solution was filtered with a paper filter to produce a clear, slightly yellow solution. The total weight of the filtered solution was 24.1 kg. The filtered solution contained 7.1 weight % Sn(II) and had a pH of 1.7.

During a third dilution stage, the solution was diluted with 6.9 kg of additional distilled water to produce a final solution. The total weight of the final solution was 31 kg. The final solution contained 60.2 g Sn(II)/L. (which corresponds to 5.5 weight % Sn(II) at a density of 1.095 g/mL) and had a pH of 1.79.

Based on the total weight of 31 kg, the final solution contained 1.71 kg Sn(II) (or 14.4 moles Sn(II)) and 2.19 kg MSA (or 23.1 moles MSA). The molar ratio of Sn(II):MSA was 14.4:23.1, or about 1:1.6. If the only $Sn_xR_z(MSA)_y$ species present in the solution was $Sn(MSA)_2$, where x is 1, y is 2, and z is 0, one would expect to see a 1:2 molar ratio of Sn(II):MSA (or x:y). However, the actual molar ratio of 1:1.6 may suggest the presence of other $Sn_xR_z(MSA)_y$ species in the solution where y is less than 2 and z is greater than 0, such as Sn(OH)MSA where x is 1, y is 1, and z is 1. This molar ratio of 1:1.6 may further suggest that about 60 weight % of the $Sn_xR_z(MSA)_y$ species are present with y equal to 2, and that about 40 weight % of the $Sn_xR_z(MSA)_y$ species are present with y equal to 1, because 60%(2)+40%(1) equals 1.6.

The final solution also contained 1.4 ppm iron (Fe), less than 1.0 ppm cobalt (Co), less than 1.0 ppm copper (Cu), less than 5 ppm nickel (Ni), less than 4 ppm lead (Pb), less than 250 ppm sulfate ($SO_4$), and less than 25 ppm chlorine (Cl).

After about 90 days, the solution was still stable with less than 0.1 weight % solids.

Example 2

Sodium Hydroxide as pH-Adjusting Agent

During a first reaction stage, tin (Sn) was reacted with an aqueous methanesulfonic acid (MSA) solution in the presence of air to produce an aqueous stannous methanesulfonate ($Sn(MSA)_2$) solution. The solution contained 21.8 weight % Sn(II) and 2.4 weight % free MSA.

During a dilution stage, 20 g of the $Sn(MSA)_2$ solution was diluted with 49.5 g of distilled water to reach a Sn(II) concentration of approximately 6.3 weight %.

During a second reaction stage, 10.4 g of a 10.6 weight % sodium hydroxide (NaOH) solution was added slowly to the diluted $Sn(MSA)_2$ solution. After filtration, the solution contained 58.8 g Sn(II)/L (which corresponds to 5.3 weight % Sn(II) at a density of 1.109 g/mL) and had a pH value of 2.1.

Based on the total weight of 75 g, the final solution contained 3.975 g Sn(II) (or 0.0335 moles Sn(II)) and 7.013 g MSA (or 0.0729 moles MSA). The molar ratio of Sn(II):MSA was 0.0335:0.0729, or about 1:2. This molar ratio of about 1:2 suggests that the only $Sn_xR_z(MSA)_y$ species present in the solution was $Sn(MSA)_2$, where x is 1, y is 2, and z is 0.

After about 30 days, the solution was still stable with less than 0.1 weight % solids.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A solution comprising at least one stannous methanesulfonate species, the solution having:
    a tin concentration of about 56 g/L to about 82 g/L; and
    a pH of about 1.50 to about 2.20,
    wherein the at least one stannous methanesulfonate species includes:
        $Sn(CH_3SO_3)_2$; and
        a second stannous methanesulfonate species including $Sn_xR_z(CH_3SO_3)_y$, wherein:
            R is a bridging atom or group;
            x is 1;
            y is less than 2; and
            z is greater than 0.

2. The solution of claim 1, wherein the tin concentration is about 58 g/L to about 62 g/L.

3. The solution of claim 1, wherein the pH is about 1.60 to about 2.00.

4. The solution of claim 1, wherein the pH is about 1.50 to about 1.70.

5. The solution of claim 1, wherein the solution has a density of about 1.1 g/mL.

6. The solution of claim 1, wherein the second stannous methanesulfonate species comprises at least one of $Sn(OH)(CH_3SO_3)$ and $Sn(O)(CH_3SO_3)$.

7. The solution of claim 1, wherein the solution comprises less than about 0.01 wt. % of chelating agents, antioxidants, stabilizers, surfactants, and complexing agents.

8. The solution of claim 1, wherein the solution comprises less than about 25 ppm of iron, cobalt, copper, nickel, and lead.

* * * * *